(12) United States Patent
Huang et al.

(10) Patent No.: US 6,977,142 B2
(45) Date of Patent: Dec. 20, 2005

(54) HIGH-THROUGHPUT TURBIDOMETRIC ASSAY FOR SCREENING INHIBITORS OF PROTEIN DISULFIDE ISOMERASE ACTIVITY

(75) Inventors: Shu-Gui Huang, Fremont, CA (US); Donna Oksenberg, Palo Alto, CA (US); Roman Urfer, Belmont, CA (US)

(73) Assignee: AGY Therapeutics, Inc., South San Francisco, CA (US)

( * ) Notice: Subject to any disclaimer, the term of this patent is extended or adjusted under 35 U.S.C. 154(b) by 108 days.

(21) Appl. No.: 10/669,382

(22) Filed: Sep. 23, 2003

(65) Prior Publication Data

US 2005/0064385 A1    Mar. 24, 2005

(51) Int. Cl.[7] ............................................. C12Q 1/00
(52) U.S. Cl. ..................... 435/4; 435/183; 435/184; 435/233; 435/7.4
(58) Field of Search ..................... 435/4, 183, 184, 435/233, 7.4

(56) References Cited

U.S. PATENT DOCUMENTS

| | | | | |
|---|---|---|---|---|
| 4,397,960 A | * | 8/1983 | Moussebois et al. | 436/512 |
| 5,989,835 A | * | 11/1999 | Dunlay et al. | 435/7.2 |
| 6,110,689 A | * | 8/2000 | Qvist et al. | 435/7.1 |

FOREIGN PATENT DOCUMENTS

| | | | | |
|---|---|---|---|---|
| WO | WO 9404185 A2 | * | 3/1994 | A61K 37/64 |
| WO | WO 200022100 A2 | * | 4/2000 | C12N 9/00 |

OTHER PUBLICATIONS

Noiva, R. Protein disulfide isomerase: the multifunctional redox chaperone of the endoplasmic reticulum. Seminars in Cell & Developmental Biology, 1999, 10: 481-493.*

Graven, KK, et al. Identification of protein disulfide isomerase as an endothelial hypoxic stress protein. Am. J. Physiol. Lung Cell Mol. Physiol., 2002, 282: L996-L1003.*

Bonfits, C. Purification of a 58-kDa protein (ER58) from monkey liver microsomes and comparison with protein-disulfide isomerase. Eur. J. Biochem., 1998, 254: 420-427.* http://www.embiosciences.com/product/539425, Mar. 1, 2005.*

Myllyla, R., et al., Protein disulfide-isomerase activity in various cells synthesizing collagen. European Journal of Biochemistry, 1983, 134(1):7-11.*

Smith, AM, et al. A high-throughput turbidometric assay for screening inhibitors of protein disulfide isomerase activity. Journal of Biomolecular Screening. 2004. 9(7): 614-620.*

Budavari, S., ed. The Merck Index 12th edition. 1996. Merck & Co., Inc. p. 551.*

Freedman et al., "Protein disulphide isomerase: building bridges in protein folding", *Trends Biochem Sci.*, (1994), 19:331-336.

Gilbert et al., "Protein Disulfide Isomerase and Assisted Protein Folding", *J. Biol. Chem.*, (1997), 272:29399-29402.

Hillson et al., "Formation and Isomerization of Disulfide Bonds in Proteins: Protein Disulfide-Isomerase", *Methods Enzymol*, (1984), 107:281-95.

Lyles et al., "Catalysis of the Oxidative Folding of Ribonuclease A by Protein Disulfide Isomerase: Dependence of the Rate on the Composition of the Redox Buffer", *Biochemistry*, (1991), 30:613-619.

Lundstrom et al., "Protein Disulfide-isomerase Is a Substrate for Thioredoxin Reductase And Has Thioredoxin-like Activity", *J Biol Chem.*, (1990), 265:9114-9120.

* cited by examiner

*Primary Examiner*—Francisco C. Prats
*Assistant Examiner*—Susan E. Fernandez
(74) *Attorney, Agent, or Firm*—Rebecca D. Taylor; Pamela J. Sherwood; Bozicevic, Field & Francis LLP (57) ABSTRACT

Methods for performing an end-point assay of protein disulfide isomerase activity. The method may be based on the enzyme-catalyzed reduction of insulin in the presence of dithiothreitol; measuring the aggregation of reduced insulin chains at 650 nm; and using hydrogen peroxide as a stop reagent.

13 Claims, 7 Drawing Sheets

HIGH-THROUGHPUT TURBIDOMETRIC ASSAY FOR SCREENING INHIBITORS OF PROTEIN DISULFIDE ISOMERASE ACTIVITY

BACKGROUND OF THE INVENTION

Protein disulfide isomerase (PDI, EC5.3.4.1) is a 57-kDa enzyme expressed at high levels in the endoplasmic reticulum (ER) of eukaryotic cells. PDI was the first enzyme known to possess the disulfide isomerase activity and has been well characterized during the past three decades. In the endoplasmic reticulum PDI catalyzes both the oxidation and isomerization of disulfides on nascent polypeptides. Under the reducing condition of the cytoplasm, endosomes and cell surface, PDI catalyzes the reduction of protein disulfides. In addition, PDI activity has been observed in other subcellular compartments such as the cytosol, as well as on the cell surface.

Folding catalysts such as PDI and peptidylprolyl isomerase accelerate slow chemical steps that accompany folding (for a review, see Freedman et al. (1994) *Trends Biochem. Sci.* 19:331–336; and Gilbert (1997) *J. Biol. Chem.* 272:29399–29402). Disulfide formation can occur quite rapidly, even before the completion of synthesis, but for some proteins disulfide formation is delayed and occurs post-translationally. During protein folding in the ER, PDI catalyzes disulfide formation and rearrangement by thiol/disulfide exchange.

A member of the thioredoxin superfamily, which also includes homologs such as ERp57, PDIp, ERp72, PDIr and ERp5, PDI has two independent but non-equivalent active sites, each with two cysteines (CGHC) that cycle between the dithiol and disulfide oxidation states. One thioredoxin domain is positioned near the N terminus, and another is poised near the C terminus. The active site disulfide is a good oxidant that directly introduces disulfides into protein substrates. The dithiol redox state is essential for catalyzing disulfide rearrangements. The necessity of having oxidized and reduced active sites for catalysis of different steps results in a redox optimum. The individual thioredoxin domains of PDI have been expressed alone, and they are catalytically active oxidants. However, neither isolated domain exhibits significant isomerase activity.

Besides its major role in the processing and maturation of secretory proteins in the endoplasmic reticulum, PDI and its homologs have been implicated in multiple important cellular processes. For example, cellular insulin degradation occurs in a sequential fashion with several identified steps. The initial degradative step occurs in endosomes with two or more cleavages in the B chain. This is followed by reduction of the disulfide bonds by PDI, or a related enzyme, yielding an intact A chain and several B chain fragments. The insulin fragments are then further cleaved, probably by multiple proteolytic systems, including lysosomes.

PDI and its homologs are also involved in the processing and maturation of various secretory and cell surface proteins in the ER following their synthesis. Several in vitro studies suggest that PDI may also function as a chaperone to assist protein folding. PDI has been shown to be up-regulated during ER stress, for example during hypoxia in endothelial cells, astrocytes, and in the cerebral cortex. These observations suggest that PDI is involved in protection of cells under stress or pathological conditions.

Besides being primarily an ER resident protein, PDI is also found on the surface of many cell types such as endothelial cells, platelets, lymphocytes, hepatocytes, pancreatic cells and fibroblasts. The reductive activity of plasma membrane PDI is required for endocytosis of certain exogenous macromolecules. The cytotoxicity of diphtheria toxin is blocked by PDI inhibitors, which block the reductive cleavage of the interchain disulfide bonds in the toxin. Similarly, PDI-mediated reductive cleavage of disulfide bonds in human immunodeficiency virus envelope glycoprotein 120 is essential for infectivity. Thus, the entry of the virus into cells can be largely prevented by PDI inhibitors. Because of these functional activities, PDI and its homologous enzymes are potentially interesting drug targets.

Although biochemical assays for measuring PDI activities have been described, they cannot be applied as high-throughput assays for screening PDI inhibitors. One assay for the oxidoreductase and isomerase activity of PDI involves measuring the oxidative refolding of scrambled ribonuclease A in the presence of GSSG/GSH. In this assay, renatured ribonuclease A is measured by the hydrolysis of cytidine 2',3'-phosphate (see Hillson et al. (1984) *Methods Enzymol* 107:281–94; and Lyles and Gilbert (1991) *Biochemistry* 30:613–619). The read-out is the UV absorbance of the product at 284 nm. Although this assay has been extensively utilized to characterize the enzyme kinetics, it cannot be applied to screen random compound library because the majority of candidate compounds absorb at 284 nm and hence would interfere in the assay.

A second assay measures catalytic reduction of insulin, as described by Lundstrom and Holmgren (1990) *J Biol Chem* 265:9114–9120. In this assay, PDI facilitates the reduction of insulin in the presence of dithiothreitol. The reduced insulin chains aggregate, and the turbidity is monitored spectrophotometrically at 650 nm. This assay, like many other turbidometric assays, measures the kinetics of product aggregation and is challenging to adapt to high-throughput screening.

In view of the functional activities of PDI and homologous enzymes, high throughput screening methods are of interest for the development of new drugs, and for assessing enzyme activity in various clinical and research settings. The present invention addresses this issue.

SUMMARY OF THE INVENTION

Methods and kits are provided for an end-point assay of protein disulfide isomerase activity. The assay can be employed to screen chemical libraries for small molecule inhibitors of PDI activity; for monitoring PDI activity in clinical situations, e.g. during hypoxia; and the like. The method is based on the enzyme-catalyzed reduction of insulin in the presence of dithiothreitol; measuring the aggregation of reduced insulin chains at 650 nm; and using hydrogen peroxide as a stop reagent. This homogenous turbidometric assay is robust, cost-effective, and can be applied to identify PDI inhibitors from random chemical libraries.

BRIEF DESCRIPTION OF THE DRAWINGS

FIG. 1. Enzyme titration. Standard reactions were performed according to Materials and Methods using PDI concentrations ($\mu$g/mL) as indicated. Absorbance at 650 nm ($OD_{650}$) was measured in five minute increments at room temperature. Data are presented as mean±standard deviation (n=4).

FIGS. 3A and 3B. Evaluation of (A) bacitracin and (B) hydrogen peroxide ($H_2O_2$) as a stop reagent. Standard reactions were performed as described in Materials and Methods. In the pre-addition experiments (A: "Pre bacitracin"; B: "Pre $H_2O_2$"), the stop reagents were added to the enzyme/insulin mixture and incubated for 10 minutes prior to the initiation of the reaction with dithiothreitol. Both reagents were able to inhibit the enzyme-catalyzed reaction and the chemical reaction. In the post-addition experiments, 2 mM bacitracin (A: "Post bacitracin") or 125 mM $H_2O_2$ (B: "Post $H_2O_2$") was added to the reaction mixture 30 minutes after initiation of the enzyme reaction as indicated by the arrows. Bacitracin (A) inhibited the enzyme reaction only slowly, whereas $H_2O_2$ (B) immediately stopped the reaction and the signal was stable for up to 28 hrs. The dotted lines represent control experiments in which the same volume of buffer instead of the stop reagent was added.

FIG. 5. Assay validation using bacitracin as an inhibitor. Dose-response assay was performed with 0.15 to 3000 µM bacitracin added 10 minutes prior to the initiation of reaction. Standard reaction was performed as described in Materials and Methods. Non-linear regression analysis revealed an $IC_{50}$=152±25 µM and Hill slope=1.2±0.2. Data presented as mean±standard deviation (n=2).

FIGS. 6A–6C. Summary of pilot high-throughput screen of 3520 single chemical compounds. High-throughput screening was performed as described in Materials and Methods. "Vehicle" controls containing equivalent amount of DMSO are in columns 1, 2 and 23. Compounds were present at a final concentration of 8.6 µM in each well of Columns 3 through 22. "Positive" control wells containing 125 mM $H_2O_2$ are in Column 24. (A) Plot of absorbance data from a typical plate. The OD measurement was performed in the light-path check mode ($OD_{650}$/cm). The solid lines represent averages of the "vehicle" and "positive" controls. The dashed lines represent 3-fold standard deviation from the respective averages. Two primary hits were identified in wells 4D and 14O of this plate. (B) A plot of the average and standard deviation for the "vehicle" and "positive" (+$H_2O_2$) controls. (C) A plot of the Z' factor for the pilot screen. Z' factor was calculated for each plate according to Z'=1–3× ($SD_{V-CTRL}$+$SD_{P-CTRL}$)/(Mean $_{V-CTRL}$-Mean $_{P-CTRL}$).

DETAILED DESCRIPTION OF THE EMBODIMENTS

Before the present methods are described, it is to be understood that this invention is not limited to particular methods described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges, subject to any specifically excluded limit in the stated range.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Methods and kits are provided for an end-point assay of protein disulfide isomerase activity. The method is based on the enzyme-catalyzed reduction of insulin in the presence of dithiothreitol; measuring the aggregation of reduced insulin chains at 650 nm; and using hydrogen peroxide as a stop reagent.

The method allows for high throughput analysis of multiple samples, for example, multiple patient samples to be screened in a diagnostic assay, or multiple potential drugs or therapeutic agents to be tested in a method of drug discovery. A high throughput assay may utilize a plurality of spatially discrete regions, which can be termed test regions and which can be wells. Each test region defines a space for the introduction of a sample containing (or potentially containing) one or more samples, candidate inhibitors, etc. In especially preferred embodiments, the invention can be used in high throughput screening for drug discovery. For example, a high throughput assay can be run in many (100 for example) 96-well or 384-well microplates at one time. Each well of a plate can have different tests performed.

Samples to be analyzed may comprise candidate PDI modulators, e.g. small molecule inhibitors, competitive inhibitors, interacting proteins, enzyme mimetics, and the like. The sample may be a biological sample, e.g. a tissue, cell line, etc. For example, cells known to upregulate PDI during hypoxia may be tested for PDI activity after a suspected hypoxic episode. Cells, e.g. endothelial cells, platelets, lymphocytes, hepatocytes, pancreatic cells and fibroblasts that express surface PDI may be tested for the presence of such biological activity. Alternatively, samples of, e.g. recombinant PDI, PDI fragments; in vitro protein synthesis reactions, and the like, may be tested.

A reaction mix for use in the methods of the invention comprises protein disulfide isomerase (PDI) or a sample suspected of comprising PDI activity; a substrate for the enzyme; a reducing agent; and assay buffer. Reactions designed to test the effect of a candidate agent will also comprise a sample of the test agent. At the completion of the reaction, a stop agent will be added. Normally the assay will include at least one positive and one negative control; and samples are preferably tested in replicate, optionally at varying concentrations. The end result is read out by determining the optical density, e.g. using a standard plate reader.

The term "PDI" is intended to refer to enzymes having protein disulfide isomerase activity, classified as EC 5.3.4.1. In this classification are included a number of enzymes, e.g. ER38_NEUCR (Q92249); ER60_SCHMA (P38658); HUMER60P (BAA11928) EUG1_YEAST (P32474); MPD1_YEAST (Q12404); PDA2_HUMAN (Q13087); PDA3_BOVIN (P38657); PDA3_HUMAN (P30101); PDA3_MOUSE (P27773); PDA3_PAPHA (P81246); PDA3_RAT (P11598); PDA4_CAEEL (P34329); PDA4_HUMAN (P13667); PDA4_MOUSE (P08003); PDA4_RAT (P38659); PDA5_HUMAN (Q14554); PDA6_ARATH (O22263); PDA6_CAEEL (Q11067); PDA6_HUMAN (Q15084); PDA6_MEDSA (P38661); PDA6_MESAU (P38660); PDA6_RAT (Q63081); PDI1_ARATH (Q9XI01); PDI1_CAEEL (Q17967); PDI1_SCHPO (Q10057); PDI2_ARATH (Q9SRG3); PDI2_CAEEL (Q17770); PDI2_SCHPO (O13811); PDI_ASPNG (Q12730); PDI_ASPOR (Q00248); PDI_BOVIN (P05307); PDI_CHICK (P09102); PDI_DATGL (Q9XF61); PDI_DROME (P54399); PDI_HORVU (P80284); PDI_HUMAN (P07237); PDI_HUMIN (P55059); PDI_MAIZE (P52588); PDI_MEDSA (P29828); PDI_MOUSE (P09103); PDI_RABIT (P21195), PDI_RAT (P04785); PDI_RICCO (Q43116), PDI_WHEAT (P52589); PDI_YEAST (P17967); TIGA_ASPNG (Q00216); and YIA5_YEAST (P40557). In many instances where the assay is performed to screen activity modulating agents, mammalian enzymes are preferred, e.g. human, murine, bovine, etc., and may be isolated from tissues, recombinantly produced, etc.

Additionally, PDI may be complexed with other polypeptides, which can modulate the enzymatic activity. For example, prolyl 4-hydroxylases (P4Hs) are enzymes residing within the endoplasmic reticulum and cytoplasm. Two catalytic alpha subunit isoforms of P4H have been cloned and characterized, both of them assembling into α2β2 tetramers, in which protein disulfide isomerase (PDI) acts as the beta subunit. This enzymatic complex regulates the hypoxia-inducible transcription factor HIFα. See, for example, Myllyharju (2003) Matrix Biol. 22(1):15–24; and Graven et al. (2002) *Am J Physiol Lung Cell Mol Physiol.* 282(5):L996–1003, herein incorporated by reference.

Where the enzyme is included as other than the test sample, the concentration is preferably optimized for background to noise signal, and to minimize costs. A preferred reaction mixture comprises sufficient enzyme to generate an optical density that can be measured accurately in microtiter wells, linear reaction kinetics, and a signal to noise ratio of at least about 4, preferably about 5 to 7. Based on the specific activity of the bovine liver enzyme (see Examples); this is accomplished with enzyme present at a concentration of at least about 0.5 µg/ml and not more than about 100 µg/ml, more usually at least about 5 mg/ml and not more than about 50 mg/ml, and preferably about 33 mg/ml.

There are multiple substrates for PDI, which may be used in the methods of the invention. Substrates of interest include, without limitation, HIV gp120, insulin, hypoxia-inducible factor, prolyl 4-hydroxylase; etc. As discussed above, prolyl 4-hydroxylase may be complexed with PDI, and may further be a substrate of PDI. HIF may be a substrate of PDI, and of prolyl 4-hydroxylase/PDI complexes. HIV gp120 increases its thiol content after interaction with a surface that enables CXCR4 binding. This increase is mediated by PDI. Disulfide bond restructuring produce conformational changes that induce fusion competence. Alternative assays of interest for PDI activity are based on detecting changes of fusion competence by HIV gp120 (see Barbouche et al. (2003) *J. Biol. Chem.* 278: 3131–3136).

A preferred substrate for the enzyme in the reaction mixture is insulin, which may be obtained from a variety of sources known to those of skill in the art, e.g. isolated from natural sources, recombinantly produced; from mammalian species including porcine, human, bovine, etc. The concentration of substrate is preferably optimized for signal to noise ratio. The chemical reduction of insulin proceeds at a slower rate than the enzymatic reaction, however at high concentrations of substrate the signal from the chemical reaction can interfere with assay results. Usually the substrate will be present at a concentration of at least about 0.075 mM and not more than about 0.3 mM, more usually present at a concentration of at least about 0.1 mM and not more than about 0.2 mM, and preferably at about 0.15 mM.

The reaction mixture comprises a reducing agent at a concentration sufficient to reduce the insulin disulfide bonds in the presence of the PDI enzyme, while not minimizing the competing chemical reaction. Reducing agents of interest include glutathione, dithiothreitol, dithioerythritol, β-mercaptoethanol, thioglycolate, and cysteine, the use of dithiothrietol (DTT) is preferred. Usually the concentration of DTT will be less then about 2 mM, and at least about 0.1 mM, preferably at a concentration of about 1 mM. Other components of the assay buffer may include buffers and chelating agents, as known in the art. For example, the reaction may be performed in 100 mM potassium phosphate; and 0.2 mM EDTA, pH 7.0. Those of skill in the art will readily be able to replace these reagents with other equivalent salts, and the like.

The reactions are sensitive to the presence of DMSO, and therefore are preferably run in less than about 2% DMSO, more preferably less than about 1% DMSO.

The reactions are run for a period of time sufficient to quantitate the PDI activity, but are stopped before the chemical reaction increases the background signal. The reactions are preferably run for at least about 15 minutes and not more than about 60 minutes, more preferably at least about 25 minutes and not more than about 45 minutes; and may be run for about 30 minutes.

Stopping the reaction is critical to the invention. The reaction must be stopped in a short period of time, using a reagent that does not interfere with the optical density, which stops the chemical as well as the enzymatic reaction; and which allows the samples to be stably stored for at least about 1 day. A preferred stop reagent is hydrogen peroxide ($H_2O_2$). This acts to oxidize the dithiothreitol, which arrests both the enzymatic and chemical reactions. $H_2O_2$ may be used at a concentration of at least about 10 mM, more usually at least about 50 mM, and preferably at least about 100 mM; and not more than about 500 mM.

The optical density of the reaction mixture is typically read at 650 nm; using methods known in the art; for high throughput assays a plate reader will generally be preferred.

Any compatible substrate surface that is transparent to light can be used in conjunction with this invention. The surface can be any of a variety of organic or inorganic materials or combinations thereof, including, merely by way of example, plastics such as polypropylene or polystyrene; silicon; (fused) silica, quartz or glass. In a preferred embodiment, the surface is the plastic surface of a multiwell plate, e.g., tissue culture dish, for example a 24-, 96-, 256-, 384-, 864- or 1536-well plate. The shape of the surface is not critical. It can, for example, be a flat surface such as a square, rectangle, or circle; a curved surface; and the like. Alternatively, a surface such as a glass surface can be etched out to have, for example, 864 or 1536 discrete, shallow wells. Alternatively, a surface can comprise regions with no separations or wells, for example a flat surface, e.g. piece of plastic or glass with individual regions that are defined by overlaying a structure that delineates the separate regions. In another embodiment, the regions can be defined as tubes or fluid control channels, e.g., designed for flow-through assays, as disclosed, for example, in Beattie et al (1995). Clin. Chem. 4:700–706. Tubes can be of any size, e.g., capillaries or wider bore tubes. The relative orientation of the test regions can take any of a variety of forms including, but not limited to, parallel or perpendicular arrays within a square or rectangular or other surface, radially extending arrays within a circular or other surface, or linear arrays, etc.

Each of the assays or procedures described below can be performed in a high throughput manner, in which a large number of samples (e.g., as many as about 864, 1036, 1536, 2025 or more) are assayed on each plate or surface rapidly and concurrently. Further, many plates or surfaces can be processed at one time. For example, in methods of drug discovery, a large number of samples, each comprising a drug candidate (e.g., a member of a combinatorial chemistry library, such as variants of small molecules, peptides, oligonucleotides, or other substances), can be added to separate wells; and assays can be performed on each of the samples. With the recent advent and continuing development of high-density microplates, robotics, improved dispensers, sophisticated detection systems and data-management software, the methods of this invention can be used to screen or analyze thousands or tens of thousands or more of compounds per day.

Compound Screening

Compound screening identifies agents that modulate function of PDI activity. Of particular interest are screening assays for agents that have a low toxicity for human cells. The term "agent" as used herein describes any molecule, e.g. protein or pharmaceutical, with the capability of altering or mimicking the physiological function of PDI. Generally a plurality of assay mixtures are run in parallel with different agent concentrations to obtain a differential response to the various concentrations. Typically one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. Test agents can be obtained from libraries, such as natural product libraries or combinatorial libraries, for example. A number of different types of combinatorial libraries and methods for preparing such libraries have been described, including for example, PCT publications WO 93/06121, WO 95/12608, WO 95/35503, WO 94/08051 and WO 95/30642, each of which is incorporated herein by reference.

Reagents that improve the efficiency of the assay, such as protease inhibitors, nuclease inhibitors, anti-microbial agents, etc. may be used. The components are added in any order that provides for the requisite activity. Incubations are performed at any suitable temperature, typically between 4 and 40° C.

Compounds that are initially identified by any of the foregoing screening methods can be further tested to validate the apparent activity. For example, a lead compound may be administered during an initial screen to an animal that serves as a model for humans and then determining the effect on PDI activity. The animal models utilized in validation studies generally are mammals. Specific examples of suitable animals include, but are not limited to, primates, mice, and rats.

Certain methods are designed to test not only the ability of a lead compound to affect PDI activity but to provide protection after the animal has undergone a condition of interest, e.g. hypoxia, infection with HIV, exposure to Diphtheria toxin, etc. for a period of time sufficient to provide a protective effect. In such methods, a lead compound is administered to the model animal (i.e., an animal, typically a mammal, other than a human). The animal is subsequently subjected to the condition of interest.

Active test agents identified by the screening methods described herein can serve as lead compounds for the synthesis of analog compounds. Typically, the analog compounds are synthesized to have an electronic configuration and a molecular conformation similar to that of the lead compound. Identification of analog compounds can be performed through use of techniques such as self-consistent field (SCF) analysis, configuration interaction (CI) analysis, and normal mode dynamics analysis. Computer programs for implementing these techniques are available. See, e.g., Rein et al., (1989) Computer-Assisted Modeling of Receptor-Ligand Interactions (Alan Liss, New York).

Once analogs have been prepared, they can be screened using the methods disclosed herein to identify those analogs that exhibit an increased ability to modulate PDI activity. Such compounds can then be subjected to further analysis to identify those compounds that appear to have the greatest potential as pharmaceutical agents. Alternatively, analogs shown to have activity through the screening methods can serve as lead compounds in the preparation of still further analogs, which can be screened by the methods described herein. The cycle of screening, synthesizing analogs and re-screening can be repeated multiple times.

Diagnostic Methods

The upregulation of PDI during hypoxia can serve as markers for diagnosing individuals that have suffered a stroke and, in prognostic evaluations, to detect individuals at risk for stroke. Knowledge of the progression stage can be the basis for more accurate assessment of the most appropriate treatment and most appropriate administration of therapeutics following a stroke. Prognostic methods can also be utilized to monitor an individual's health status prior to and after a stroke, as well as in the assessment of the severity of the stroke and the likelihood and extent of recovery. In general, such diagnostic and prognostic methods involve detecting an elevated level of PDI activity using the methods described herein. More specifically, the diagnostic and prognostic methods disclosed herein involve obtaining a sample from an individual and determining at least qualitatively, and preferably quantitatively, the level of PDI activity in the sample. Usually this determined value or test value is compared against some type of reference or baseline value.

The term "stroke" broadly refers to the development of neurological deficits associated with impaired blood flow to the brain regardless of cause. Potential causes include, but are not limited to, thrombosis, hemorrhage and embolism. Current methods for diagnosing stroke include symptom evaluation, medical history, chest X-ray, ECG (electrical heart activity), EEG (brain nerve cell activity), CAT scan to assess brain damage and MRI to obtain internal body visuals. Thrombus, embolus, and systemic hypotension are among the most common causes of cerebral ischemic episodes. Other injuries may be caused by hypertension, hypertensive cerebral vascular disease, rupture of an aneurysm, an angioma, blood dyscrasias, cardiac failure, cardiac arrest, cardiogenic shock, septic shock, head trauma, spinal cord trauma, seizure, bleeding from a tumor, or other blood loss.

By "ischemic episode" is meant any circumstance that results in a deficient supply of blood to a tissue. When the ischemia is associated with a stroke, it can be either global or focal ischemia, as defined below. The term "ischemic stroke" refers more specifically to a type of stroke that is of limited extent and caused due to blockage of blood flow. Cerebral ischemic episodes result from a deficiency in the blood supply to the brain. The spinal cord, which is also a part of the central nervous system, is equally susceptible to ischemia resulting from diminished blood flow.

By "focal ischemia," as used herein in reference to the central nervous system, is meant the condition that results from the blockage of a single artery that supplies blood to the brain or spinal cord, resulting in damage to the cells in the territory supplied by that artery.

By "global ischemia," as used herein in reference to the central nervous system, is meant the condition that results from a general diminution of blood flow to the entire brain, forebrain, or spinal cord, which causes the death of neurons in selectively vulnerable regions throughout these tissues. The pathology in each of these cases is quite different, as are the clinical correlates. Models of focal ischemia apply to patients with focal cerebral infarction, while models of global ischemia are analogous to cardiac arrest, and other causes of systemic hypotension.

Stroke can be modeled in animals, such as the rat (for a review see Duverger et al. (1988) *J Cereb Blood Flow Metab* 8(4):449–61), by occluding certain cerebral arteries that prevent blood from flowing into particular regions of the brain, then releasing the occlusion and permitting blood to flow back into that region of the brain (reperfusion). These focal ischemia models are in contrast to global ischemia models where blood flow to the entire brain is blocked for a period of time prior to reperfusion. Certain regions of the brain are particularly sensitive to this type of ischemic insult. The precise region of the brain that is directly affected is dictated by the location of the blockage and duration of ischemia prior to reperfusion. One model for focal cerebral ischemia uses middle cerebral artery occlusion (MCAO) in rats. Studies in normotensive rats can produce a standardized and repeatable infarction. MCAO in the rat mimics the increase in plasma catecholamines, electrocardiographic changes, sympathetic nerve discharge, and myocytolysis seen in the human patient population.

Kits

Another embodiment of the invention is a kit useful for the detection of PDI activity, or PDI modulatory activity in a sample, which kit comprises: a container comprising at calibrated PDI enzyme, for use as a control and/or as a reagent in the assay; a PDI substrate, usually insulin; and stop buffer for the reaction. Kits may further comprise one or more of a buffer for performing the reaction; a container of reducing agent; known inhibitors of the reaction as a control; microwell plates for performing the assay; and the like.

In one embodiment, there is provided the reagents listed above, and a set of instructions. The instructions can include, for example (but are not limited to), a protocol for performing the assay, and of methods, e.g., to quantitate, normalize, "fine-tune" or calibrate assays. The instructions can encompass any of the parameters, conditions or embodiments disclosed in this application, all of which can be performed routinely, with conventional procedures, by one of skill in the art.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Experimental

Materials and Methods

Protein disulfide isomerase (PDI) from bovine liver (Catalog number P3818), insulin from bovine pancreas (Catalog number 14011), dithiothreitol (Catalog number D9779), $H_2O_2$ (Catalog number H6520) and bacitracin (Catalog number B0125) were purchased from Sigma. A stock solution of 1.6 mM insulin was prepared by dissolving insulin in 0.1 N HCl. Clear polystyrene 384-well assay plates were obtained from Greiner (Catalog number 781101). All reagents used in this study were of analytical grade.

The assay utilized the method according to Bonfils (1998) *Eur J Biochem* 254:420–427, but was miniaturized in 384-well plates. The assay buffer consisted of 100 mM potassium phosphate and 0.2 mM EDTA, pH 7.0. In a standard room temperature assay, insulin from a 1.6 mM stock solution and PDI from a 5 mg/mL stock were added to final concentrations of 0.16 mM and 33 ug/mL in assay buffer, respectively. Aliquots of the reaction mixture were then added at 30 $\mu$L per well to 384-well assay plates. To initiate the reaction, 5 $\mu$L of 7 mM dithiothreitol (final concentration 1 mM) was added and quickly mixed. The enzyme reaction was monitored at 650 nm on a SpectraMax Plus plate reader (Molecular Devices, Sunnyvale, Calif.).

For high-throughput screening, a Biomek 2000 liquid handling system (Beckman-Coulter, Palo Alto, Calif.) was used to add 5 $\mu$L of 1 M positive control $H_2O_2$ to each well in column 24 of the assay plates. Then a Biomek FX384 pipettor (Beckman-Coulter, Palo Alto, Calif.) was programmed to automate the subsequent additions. The pipettor aspirated 29 $\mu$L of the enzyme/substrate mixture, applied a 0.5-$\mu$L air gap, dipped into DMSO to wash the pipette tip exterior, pipetted 1 $\mu$L of 300 $\mu$M compound, and then dispensed the entire volume into the assay plate. After the dispense step, the compound was mixed well with the enzyme and substrate. Following a 10 min pre-incubation, 5 $\mu$L of 7 mM dithiothreitol was dispensed into the reaction wells. This was followed immediately by a mixing step, in which 20 $\mu$L of the mixture was aspirated and dispensed twice in the well. The reaction was allowed to proceed for 30 min and stopped by adding 5 $\mu$L of 1 M $H_2O_2$ (final concentration 125 mM) to each well. The optical density of each well was measured at 650 nm on the SpectraMax Plus plate reader.

For data analysis, the results are presented as mean±standard deviation. Dose-response curves were fitted by least square regression using Prism (version 3.03). The Z' factor was calculated according to Zhang et al. (1999) *J Biomol Screen* 4:67–73.

RESULTS AND DISCUSSION

Figure 1:
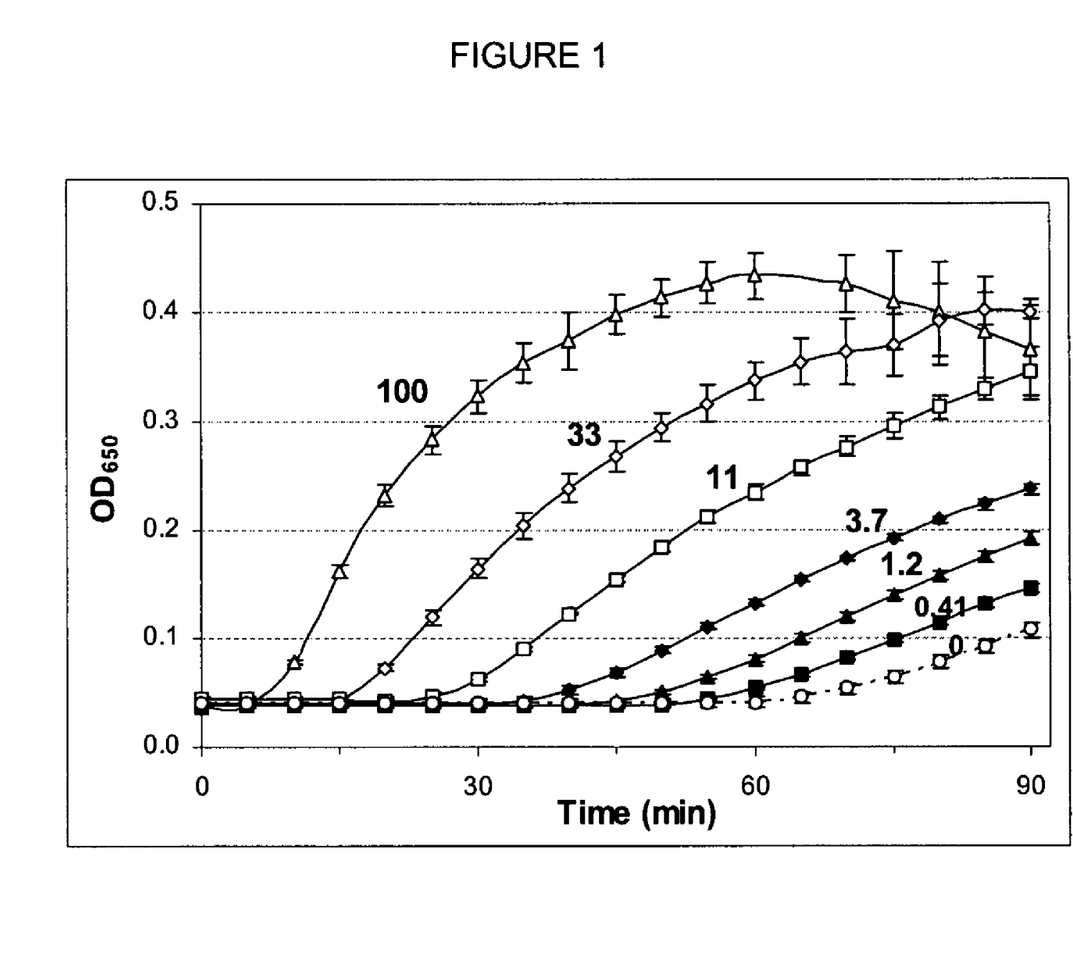

The catalytic reduction of insulin by PDI in the presence of dithiothreitol resulted in formation of reduced insulin chains. The turbidity due to the precipitation of the reduced polypeptides was measured at 650 nm. FIG. 1 shows typical reaction kinetics obtained in 384-well microtiter plates. In all cases, we observed an initial lag phase followed by an exponential increase in turbidity indicative of the formation of precipitated insulin chains. This biphasic kinetics was in accordance with previous observations.

Adaptation of this assay for high-throughput screening required overcoming several obstacles. The first challenge was miniaturizing the cuvette assay to a microtiter plate assay, in which the reaction volume is typically 50 $\mu$L or less. This can be particularly challenging because the absorbance depends linearly on optical length. Initial experiments showed that in a 40-$\mu$L assay, an $OD_{650}$ of up to 0.5 could be observed in 384-well plates. This signal amplitude allows a significant signal to noise ratio under the assay conditions.

As shown in FIG. 1, the onset of turbidity depended strongly on PDI concentration. In the absence of any PDI, there was no observable turbidity on incubation for up to 70 min. Aggregation occurred slowly after 70 min, presumably due to slow chemical reduction of insulin by dithiothreitol. This reductive reaction was accelerated by PDI, such that at 100 $\mu$g/mL PDI, significant turbidity was observed within minutes after the addition of dithiothreitol. An enzyme concentration of 33 $\mu$g/mL was selected for subsequent assays because (1) the amount of enzyme (1 $\mu$g per well) and hence the costs were acceptable for HTS campaigns and (2) the reaction resulted in an OD around 0.15 to 0.20 at 30 min, which can be measured accurately in microtiter wells. Under the experimental conditions, a signal to noise ratio of 5- to 7-fold was observed, suggesting that this assay could potentially be adapted for HTS. Furthermore, the reaction kinetics was linear for up to 30 min. There was also a good separation in the kinetics between the PDI-catalyzed reaction and the chemical reaction, the latter occurring only after 70 min.

Figure 2:
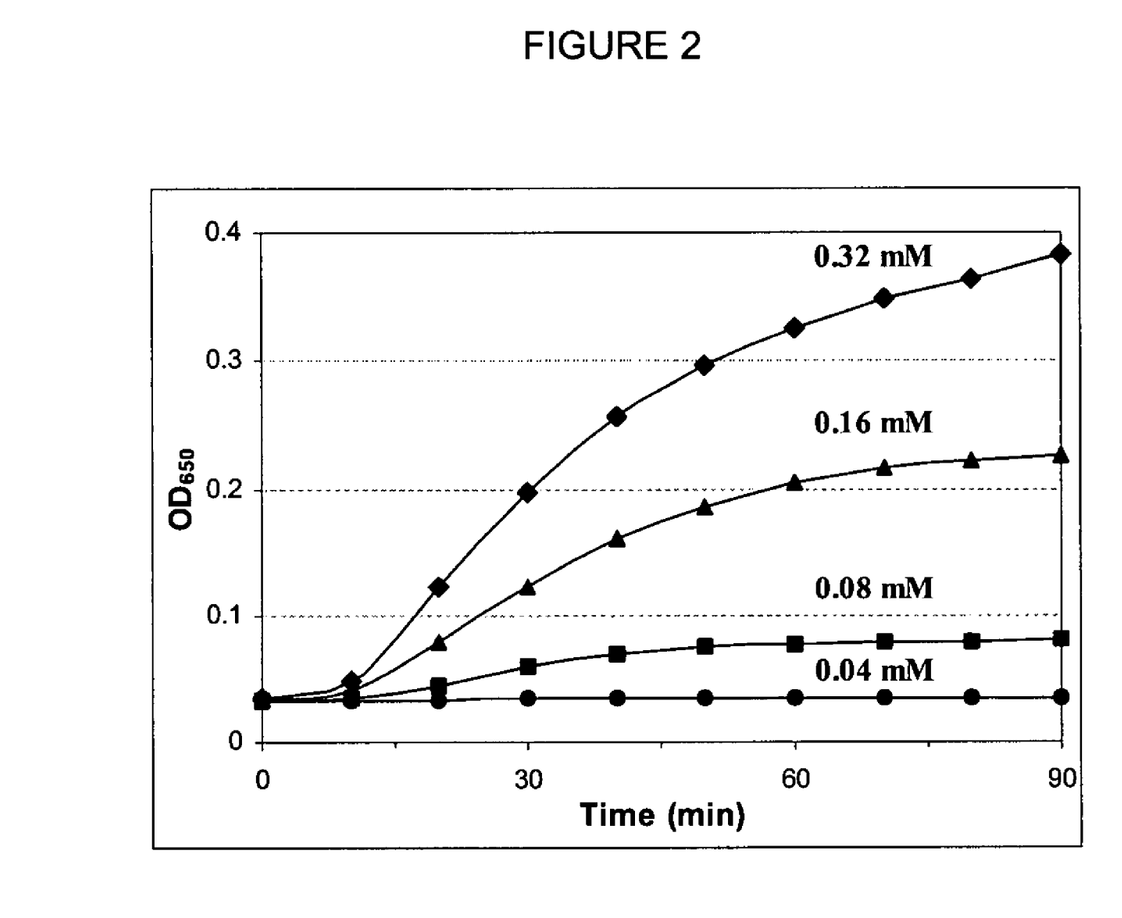
FIG. 2. Optimization of insulin concentration. Standard reactions were performed according to Materials and Methods using insulin concentrations as indicated.

The insulin concentration to be used in the assays was determined for optimal signal to noise ratio. FIG. 2 illustrates the enzyme kinetics measured in the presence of 0.04 to 0.32 mM insulin with dithiothreitol concentration held at 1 mM. While the reductive reaction proceeded faster with increasing insulin concentration as expected, the chemical reaction was also accelerated, such that at 0.32 mM insulin, significant precipitation occurred at 40 min. Because an increase in the basal level turbidity due to accelerated chemical reaction would significantly reduce the signal to noise ratio, these results suggest that 0.16 mM of insulin was an optimal concentration. Varied dithiothreitol concentrations were tested in order to optimize the assay performance. Dithiothreitol remarkably accelerated the chemical reaction at concentrations >2 mM. Therefore, 1 mM dithiothreitol was chosen for use in the assays.

Conversion of the kinetic assay into an end-point assay was necessary, because the latter can be readily automated for high-throughput screening. For this purpose, a reagent that could effectively terminate the reaction without altering the turbidity signal was required. Furthermore the reagent should be cost-effective to minimize expense for large scale HTS campaigns.

Figure 3A:
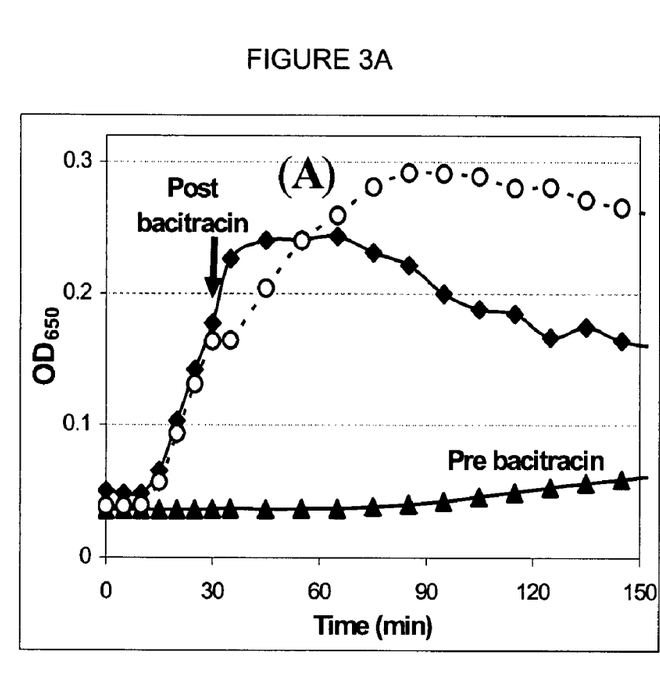

The antibiotic agent bacitracin has been reported to be an inhibitor of PDI. In FIG. 3A bacitracin was evaluated as a stop reagent. Standard reactions were run for 30 min and then 2 mM bacitracin was added to terminate the reaction. Following the addition of bacitracin, the signal still increased and then declined slowly to a plateau at $OD_{650}$=0.16 after 2 hours, at which time the chemical reaction in the control experiment had resulted in a similar signal. Therefore bacitracin is a slow inhibitor and was not suitable as a stop reagent. However, when bacitracin was incubated with the enzyme prior to the addition of dithiothreitol, it dramatically inhibited the enzyme reaction (FIG. 3A).

Figure 3B:
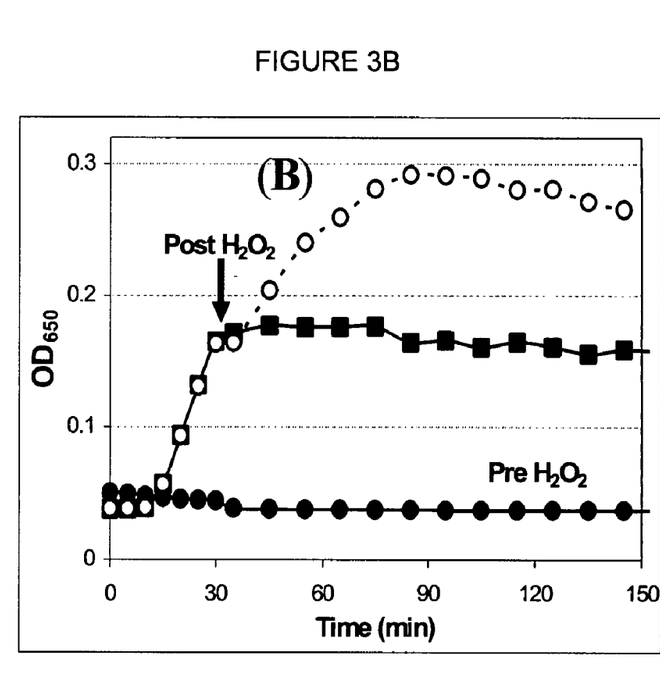

Hydrogen peroxide ($H_2O_2$) was tested. It oxidized the dithiothreitol and arrested the reaction by depletion of the reductant dithiothreitol. As shown in FIG. 3B, addition of 125 mM $H_2O_2$ was able to stop the reaction immediately and the signal stayed constant at $OD_{650}$=0.17 for up to 28 hours. This finding demonstrated that $H_2O_2$ did not interfere with the insulin aggregates and that, considering a reading time of 2 min/plate on the absorbance reader, the signal stability would allow screening of at least 100 plates per day. Preincubation of $H_2O_2$ terminated both the enzyme reaction and the chemical reaction, such that the control signal (Pre $H_2O_2$) is the same as the control signal ($OD_{650}$=0.04) in the absence of the enzyme prior to the chemical reaction. Thus 125 mM $H_2O_2$ was determined as optimal for terminating the reaction. Furthermore, the cost of $H_2O_2$ is 100-fold lower than that of bacitracin.

Figure 4:
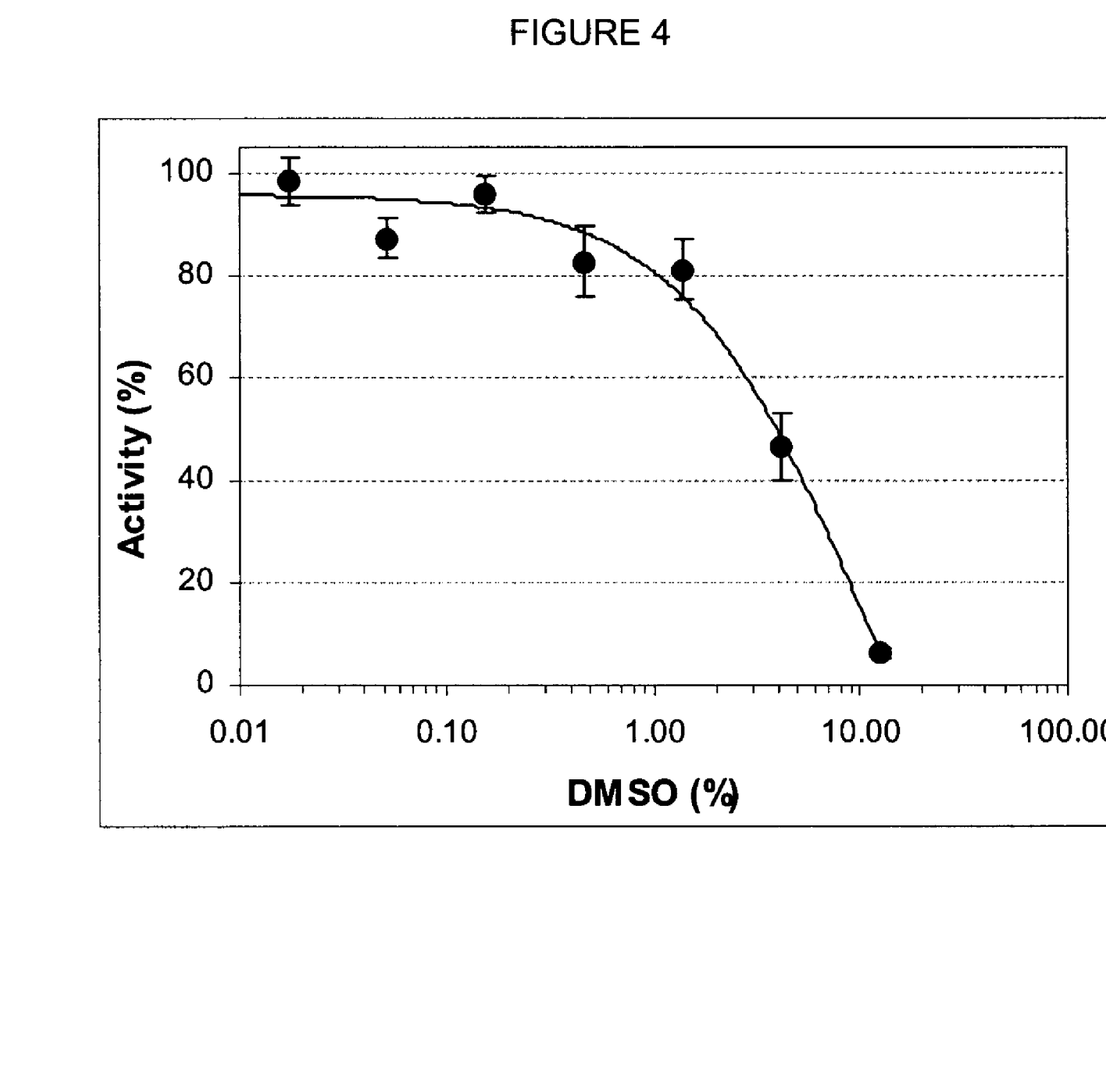
FIG. 4. Effects of DMSO on the turbidometric assay. Standard reaction was performed in the presence of 0.2% to 10% DMSO. DMSO caused a decrease in the absorbance signal presumably due to dissolution of the insulin aggregates. The assay tolerated up to 3% DMSO. Data presented as mean±standard deviation (n=4).

Because all screening samples were dissolved in DMSO, the DMSO tolerance of this assay was determined. For this purpose, the standard enzyme reaction was carried out in the presence of 0 to 10% DMSO. This assay was not significantly affected by up to 2% DMSO, but the signal declined significantly when DMSO was present at greater than 3% (FIG. 4). The high DMSO sensitivity is most likely due to dissolution of insulin aggregates by DMSO, rather than the sensitivity of PDI to DMSO per se.

Figure 5:
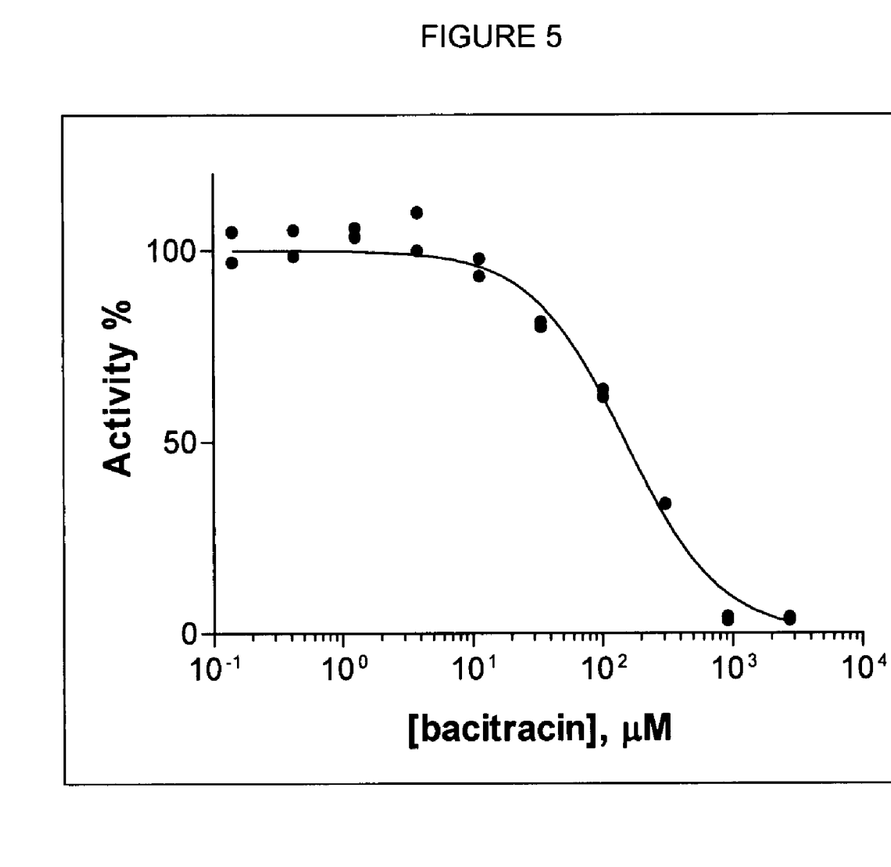

To validate the turbidometric assay, the potency of bacitracin as an inhibitor of PDI activity was measured. Bacitracin has been reported previously as a PDI inhibitor. In the insulin reduction assay, the $IC_{50}$ of bacitracin was measured to be about 200 µM. A dose-response assay for bacitracin using the high-throughput assay was determined. FIG. 5 shows that bacitracin inhibited PDI activity in a dose-dependent manner with an $IC_{50}$ of 152 µM and Hill slope of 1.2. The $IC_{50}$ is in good agreement with that reported in the literature, suggesting that this HTS assay is validated.

Figure 6A:
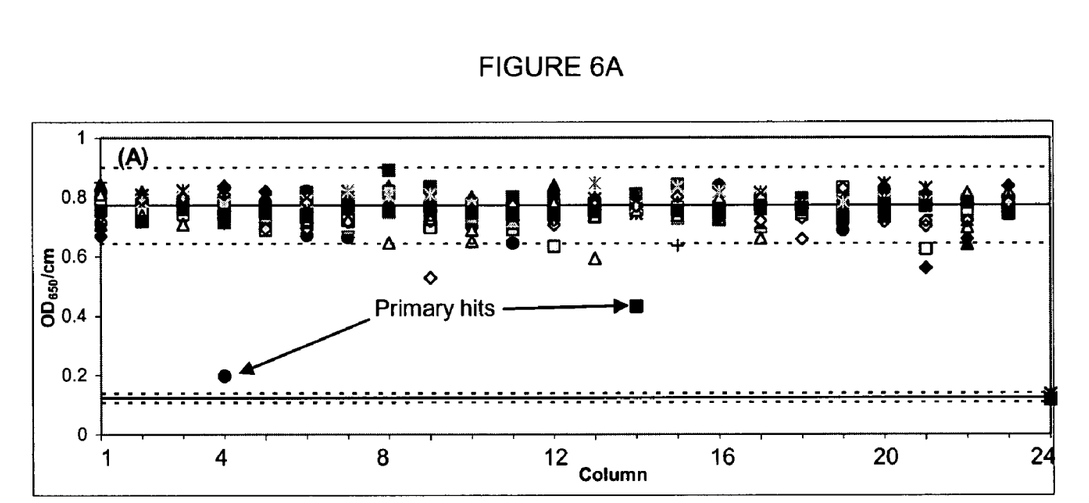
Figure 6B:
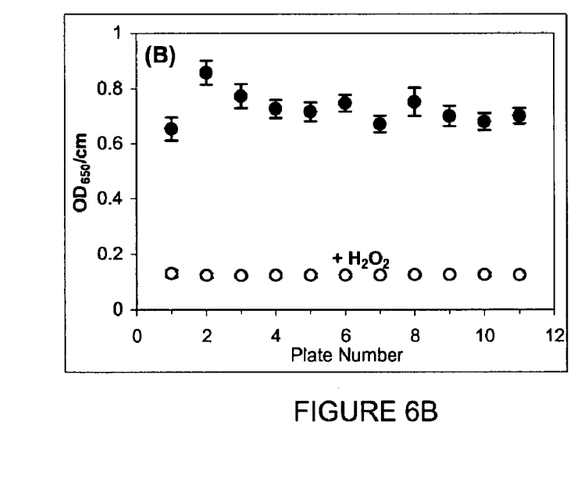
Figure 6C:
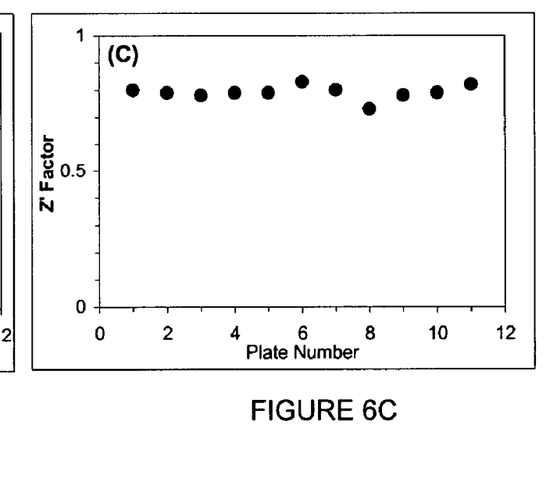
Figure 7:
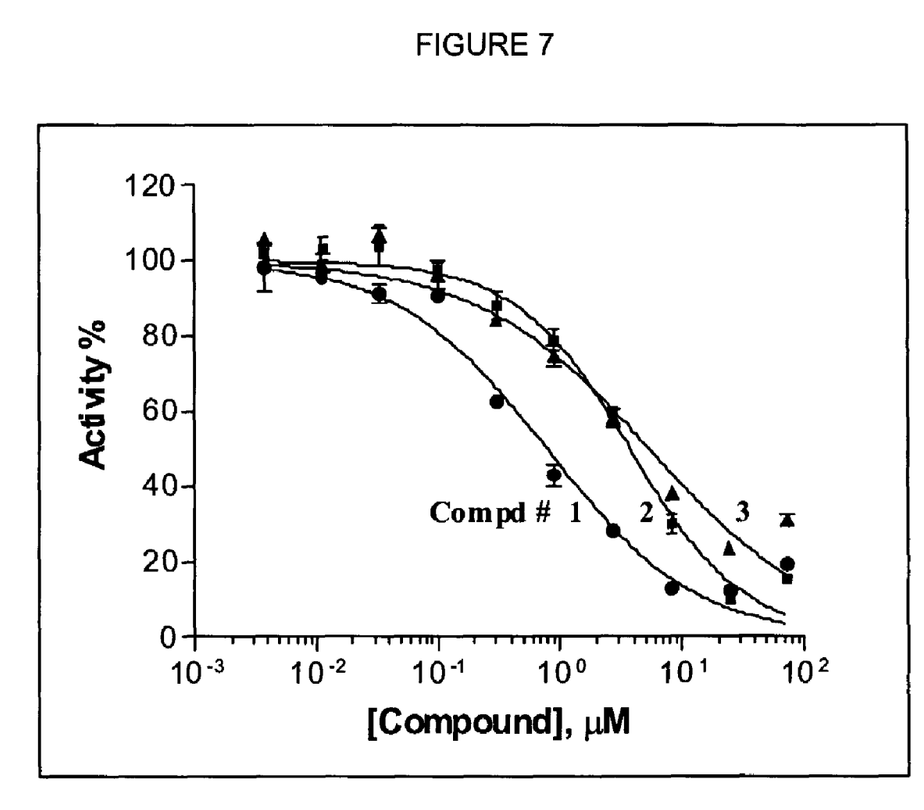
FIG. 7. Dose response curves of 3 compounds identified from the pilot screen. The inhibitors were incubated with the enzyme and insulin for 10 minutes prior to the initiation of reaction with dithiothreitol. All compounds inhibited the enzyme reaction in a dose-dependent manner with $IC_{50}$ values of 0.78 µM for compound #1, 3.7 µM for compound #2 and 5.3 µM for compound #3 and Hill slopes of −0.76, −0.94 and −0.78 respectively. Data presented as mean±standard deviation (n=2).

The assay was automated, and a pilot screen was run in order to evaluate the performance of this assay under HTS conditions. For assay automation, we used a Biomek 2000 liquid handling instrument to add the positive controls, and a Biomek FX384 pipettor for all subsequent pipetting steps. First, the positive control reagent $H_2O_2$ was added to Column 24 of each assay plate. A mixture containing PDI, insulin and compound was added to all wells in the plate. The reaction was initiated by the addition of dithiothreitol and terminated by the stop reagent $H_2O_2$. For the pilot HTS, we screened eleven 384-well compound plates that contained 3,520 single synthetic small molecule compounds. The results of the pilot screen are summarized in FIG. 6. FIG. 6A shows the data from one of the pilot compound plates. The "vehicle" or DMSO controls were in all wells in columns 1, 2 and 23. "Positive" controls (+$H_2O_2$) were added in Column 24 of each plate. Compounds were present in wells from Column 3 to Column 22. A signal to noise ratio of 5 to 7-fold was calculated from the averages of the "vehicle" and "positive" controls. A primary hit was defined as a compound that displayed 50% or greater inhibition of the enzyme activity under the assay conditions. In this plate, two primary hits were found in Column 4 Well D (89% inhibition) and in Column 14 Well O (52% inhibition). The coefficient of variance (CV %) was generally lower than 7% for the controls wells. The average and standard deviation of the "vehicle" and "positive" wells were plotted for each of the 11 plates in FIG. 6B. The Z' factor (FIG. 6C) was around 0.8, indicating that this assay can be used to generate high quality screen data from chemical libraries. From the pilot screen of the 3,520 random synthetic compounds, we identified 7 primary hits. The hit-rate was about 0.2%. We directly performed a dose-response study to measure the $IC_{50}$ of these hits. FIG. 7 shows the dose-response data for three potent compounds. The $IC_{50}$ was 0.78 µM for compound #1, 3.7 µM for compound #2 and 5.3 µM for compound #3. The Hill slope was between −0.75 and −0.94, close to the expected value of −1.

In summary, we have developed a high-throughput turbidometric assay for screening inhibitors of PDI activity. The assay is homogenous, robust and cost-effective. The throughput is projected to 32,000 compounds or 100 plates per day. The material costs were estimated to be 3 cents/well. Its feasibility as a high-throughput assay for screening PDI inhibitors from a random chemical library has been demonstrated.

What is claimed is:

1. A method of performing an end point assay for protein disulfide isomerase (PDI) activity, the method comprising:
   combining in a reaction mixture: a source of PDI activity; a substrate for PDI activity; and a reducing agent, wherein a plurality of said assays are performed in parallel;
   incubating said reaction mixture for a period of time sufficient to reduce disulfide bonds present in said substrate;
   stopping said reaction with hydrogen peroxide; and
   taking the optical density measurement of said reaction mixture, wherein an increase in said optical density as compared to said optical density of a negative control is indicative of the presence of PDI activity.

2. The method according to claim 1, wherein said substrate is selected from the group consisting of insulin and HIV gp120.

3. The method according to claim 2, wherein said substrate is present at a concentration of from 0.075 to 0.3 mM.

4. The method according to claim 1, wherein said reducing agent is dithiothreitol (DTT).

5. The method according to claim 4, wherein said DTT is present at a concentration of from 0.1 to 2 mM.

6. The method according to claim 1, wherein said hydrogen peroxide is added to a final concentration of from 10 to 500 mM.

7. The method according to claim 1, wherein said reaction mixture is incubated for a period of time from 15 to 60 minutes.

8. The method according to claim 1, wherein said optical density is read at 650 nm.

9. The method according to claim 1, wherein said reaction mixture comprises less than 2% dimethyl sulfoxide.

10. The method according to claim 1, wherein said assays are performed in a microtiter plate.

11. The method according to claim 1, wherein said source of PDI activity is a biological sample.

12. The method according to claim 1, wherein a recombinantly produced source of PDI activity is combined with said reaction mixture, and said reaction mixture further comprises a sample comprising a candidate PDI modulating agent.

13. The method according to claim 12, wherein said PDI is provided at a concentration of 0.5 µg/ml to 100 µg/ml.

* * * * *